United States Patent [19]
Frey

[11] Patent Number: 5,463,134
[45] Date of Patent: Oct. 31, 1995

[54] PARAFFIN TREATING PROCESS FOR MERCAPTAN AND OLEFIN REMOVAL

[75] Inventor: Stanley J. Frey, Palatine, Ill.

[73] Assignee: UOP, Des Plaines, Ill.

[21] Appl. No.: 238,606

[22] Filed: May 4, 1994

[51] Int. Cl.$^6$ .................................................. C07C 319/16
[52] U.S. Cl. ..................... 568/59; 568/697; 208/189; 208/192
[58] Field of Search .................... 568/59, 697; 208/189, 208/197

[56] References Cited

U.S. PATENT DOCUMENTS

| | | | |
|---|---|---|---|
| 4,465,870 | 8/1984 | Herskovits | 568/697 |
| 4,775,462 | 10/1988 | Imai et al. | 208/189 |
| 5,254,748 | 10/1993 | Hensley et al. | 568/697 |
| 5,304,683 | 4/1994 | Sattich | 568/59 |
| 5,321,163 | 6/1994 | Hickey et al. | 568/59 |

OTHER PUBLICATIONS

K. L. Rock. "Reduce the Cost of Producing TAME", Presented at the 1994 National Petroleum Refiners Association Annual Meeting, Mar. 20–22, 1994, pp. 1–6.

Primary Examiner—James H. Reamer
Attorney, Agent, or Firm—Thomas K. McBride; John F. Spears, Jr.

[57] ABSTRACT

Contaminants such as mercaptans, oxygenates and olefins are removed from paraffin-rich feed streams through the use of catalytic distillation performed using an acid catalyst such as a sulphonated resin in the substantial absence of hydrogen. The mercaptans are reacted with the olefins to form less volatile thioethers removed as part of a net bottoms stream with the treated paraffins being removed as the overhead stream.

10 Claims, 1 Drawing Sheet

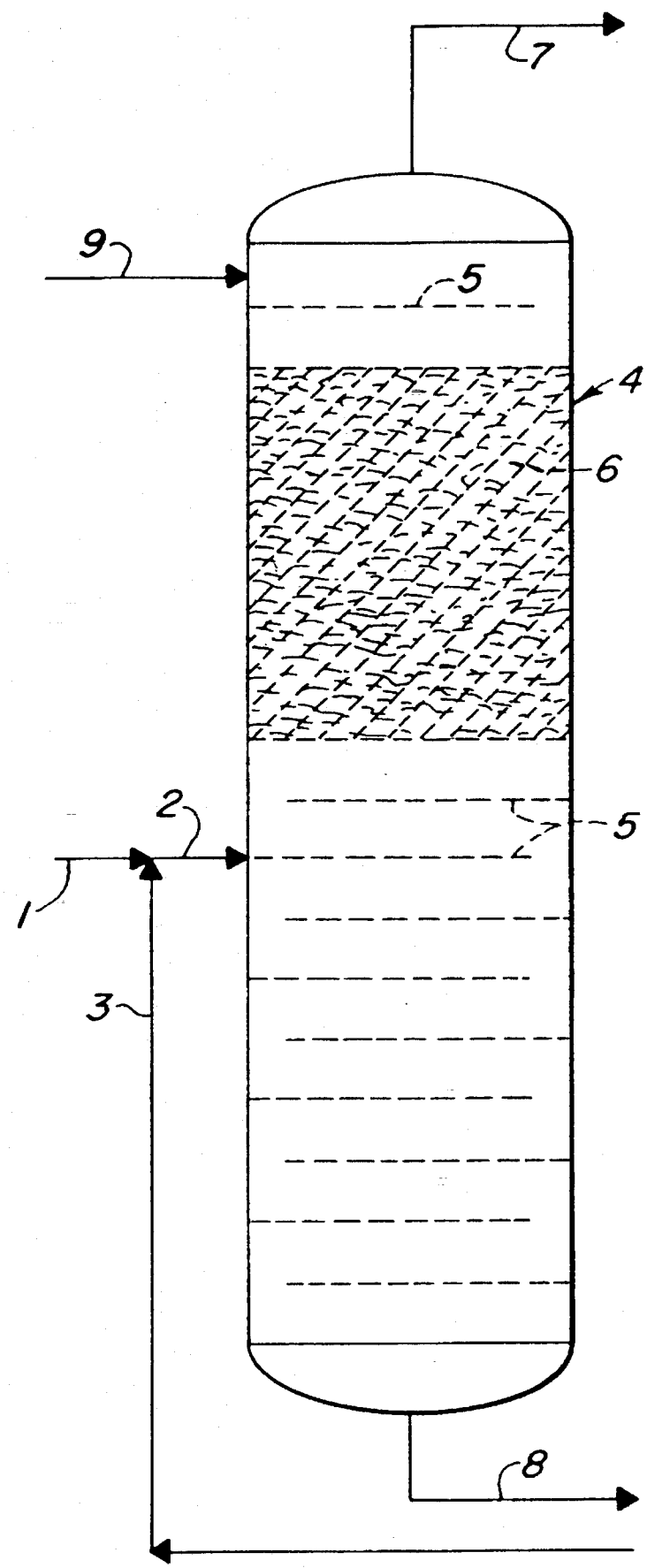

PARAFFIN TREATING PROCESS FOR MERCAPTAN AND OLEFIN REMOVAL

BACKGROUND OF THE INVENTION

Large quantities of paraffins are consumed in commercial processes which produce motor fuel alkylate by alkylation reactions and produce ethers including methyl tertiary butyl ether (MTBE) by etherification reactions. The production of these compounds is often a multistep process which requires recycling various intermediate paraffin-containing process streams. For instance a large etherification complex will normally contain a catalytic paraffin dehydrogenation unit and a catalytic isomerization unit in addition to the etherification unit. The incomplete conversion in these zones requires recycling paraffins recovered from the effluent of the etherification zone to the isomerization and dehydrogenation zones. This recycle stream will contain small amounts of nonparaffinic materials such as water or oxygenates including the product ether and feed alcohol. These nonparaffinic compounds are often detrimental to the catalysts and adsorbents employed in the next processing unit and it is necessary to remove them by some means.

The fresh feed stream to a process unit or to an overall processing complex may also contain compounds which are contaminants in the sense that they are injurious to the catalyst used in the process. In the case of a paraffinic fresh feed stream produced in a refinery these are likely to be indigenous sulfur compounds such as mercaptans.

1. Field of the Invention

The invention relates to a process for removing undesired contaminants from paraffinic feed streams destined for hydrocarbon conversion process units. More specifically the invention relates to a process for removing mercaptans, oxygenates and olefins from a paraffin rich stream through the use of catalytic distillation. The invention is directly concerned with a process to deliver pure $C_4$ paraffins to a stand-alone isomerization unit or to an isomerization zone used in an etherification complex and which eliminates butenes, alcohol, water and mercaptans from the feed stream to the isomerization zone.

2. Related Art

An overall process flow for an etherification complex receiving an external feed stream and having a recycle stream from the etherification unit is shown in U.S. Pat. No. 4,465,870 issued to L. E. Herskovits. This reference employs adsorption to remove the small amounts of oxygenates such as the product ether and feed alcohol present in the $C_4$ recycle or "raffinate" stream recovered from the effluent of the etherification zone to avoid deleterious impacts on the catalysts in the isomerization and/or dehydrogenation reaction zones of the overall complex. This reference also shows the admixture of the fresh butane feed stream, which is the potential source of mercaptans and olefins, into the recycled raffinate.

U.S. Pat. No. 4,775,462 issued to T. Imai and J. C. Bricker describes a non-oxidative method for the sweetening of a sour hydrocarbon fraction. The hydrocarbon fraction is contacted with an acid-type catalyst in the presence of an unsaturated hydrocarbon to convert the mercaptans to thioethers. The applicable catalysts are described as including polymeric sulfonic acid resins and butenes are indicated as suitable unsaturated hydrocarbons for the sweetening of LPG streams.

A paper entitled *Reduce the Cost of Producing TAME* by K. L. Rock presented at the 1994 National Petroleum Refiners Association annual meeting describes two treatment methods for the olefinic hydrocarbon feed stream which is to be charged to an etherification zone. One such method is to contact the feedstream with an aqueous caustic solution and to the convert the extracted mercaptans to disulfides via an oxidative reaction. The second method, described on page 4, involves the reaction of the reaction of diolefins present in the feed stream with the mercaptans which are also present in the feed stream to form a sulfide. This is performed in the presence of hydrogen used for olefin saturation.

BRIEF SUMMARY OF THE INVENTION

The invention is a process for treating paraffin-rich hydrocarbon streams to reduce the levels of mercaptans and olefinic hydrocarbons in the hydrocarbon stream. The subject invention has the advantages of greatly reducing the size and complexity of the equipment needed to remove these compounds from the paraffin stream and therefore greatly reduces the capital cost of this operation. The invention also eliminates the need to use treating agents such as "caustic" (aqueous sodium hydroxide solution) and to dispose used caustic which are inherent in the prior art oxidative mercaptan removal processes.

One broad embodiment of the invention may be characterized as a process for the removal of mercaptans from a paraffin-rich stream which comprises the steps of passing a feed stream, comprising one or more $C_3$ to $C_6$ feed paraffins, and also comprising at least one $C_1$ to $C_3$ mercaptan and an olefinic hydrocarbon at a concentration of less than 5 volume % each, with the olefinic hydrocarbon having the same number of carbon atoms per molecule as the feed paraffin(s) into a catalytic distillation column operated at conditions which effect the separation of the compounds present in the column into a net overhead stream, which comprises substantially all of the paraffins which enter the column in the feed stream, and a net bottoms stream which comprises sulfur compounds and dimers of the olefinic hydrocarbons present in the feed stream; contacting the compounds present in the feed stream in the substantial absence of hydrogen with a bed of catalyst located in the catalytic distillation column and maintained at conditions which effect the production of thioethers by the reaction of mercaptans present in the feed stream with olefinic hydrocarbons present in the feed stream and the dimerization of olefinic hydrocarbons; and, removing said net bottoms stream and said net overhead stream from the column.

BRIEF SUMMARY OF THE DRAWING

The drawing is a diagram of a catalytic distillation column 4 having catalyst in zone 6 for the reaction of mercaptans and olefins present in the feed stream of line 1.

DETAILED DESCRIPTION AND PREFERRED EMBODIMENTS

As previously stated, it is often necessary to remove various low level contaminants from paraffinic feed and recycle streams charged to hydrocarbon conversion units. This may be needed in the case of an integrated process for the production of ethers. It may also be necessary to remove mercaptans and olefinic hydrocarbons from the feed stream of a standalone or once-through hydrocarbon conversion unit. For instance paraffinic $C_4$ feedstreams to an isomerization, dehydrogenation or etherification unit which are derived from a fluidized catalytic cracking (FCC) unit will normally contain some mercaptans and olefins. Several different mercaptans including $C_1$, $C_2$, and $C_3$ mercaptans can be present simultaneously. These feed streams may be passed into once-through etherification units or integrated etherification complexes and will introduce the mercaptans and olefins into either situation. In the case of an integrated etherification unit the recycle $C_4$ stream, often referred to as the $C_4$ raffinate, is normally recovered from the effluent of the etherification reactor. This effluent is subjected to a fractionation operation to remove the higher boiling ethers and a water wash intended to recover the feed alcohol. The remaining $C_4$ raffinate stream will normally contain some residual alcohol which is not removed by the water wash and will also contain some water picked up in the water washing step. It will also contain a small amount of the product ether such as MTBE and by product oxygenates such as dimethyl ether.

It is an objective of this invention to provide a method for treating the $C_4$ feed streams to an etherification unit to remove mercaptans and olefinic hydrocarbons. It is a further objective of the subject process to provide an improved method for treating the combined paraffin recycle and feed streams of an integrated etherification complex to remove oxygenates and/or water. Yet another objective of the invention is the elimination or reduction of the olefin content of a light paraffin stream in a catalytic distillation column without the presence of hydrogen in the column or in the overhead vapor of the column.

The subject invention achieves these objectives by the use of a catalytic distillation column containing a bed of catalyst which promotes the reaction of the various contaminants and their conversion into compounds which can be blended into motor fuel. More specifically the subject invention employs catalytic distillation to effect the reaction of the mercaptans in the paraffinic stream with olefinic hydrocarbons to produce thioethers.

The subject process eliminates olefins from the feed stream without the use of hydrogen. This is extremely advantageous when it is desired to perform mercaptan and olefin reduction via catalytic distillation using an existing splitter fractionation column. Such columns, designed for splitting a feed into two hydrocarbon fractions, do not have an overhead vapor system designed to handle any significant amount of non-condensible gases such as hydrogen. It would be quite costly to revamp the overhead system. In addition hydrogen would become dissolved in the overhead liquid of the column, which may adversely affect the operation of downstream facilities and conversion zones. It is therefore greatly beneficial to be able to remove, or at least greatly reduce, the olefin level of the column feed without the use of hydrogen.

The overall process flow of the subject invention can be best described by reference to the Drawing. The Drawing is a simplified flow diagram of a catalytic distillation column 4 which receives a combined feed stream carried by line 2 which comprises the admixture of the fresh butane feed stream of line 1 and the recycle butane stream of line 3. The fresh butane stream of line 1 contains some mercaptans and butenes and a small (less than 3 mole %) amount of $C_5$ hydrocarbons. The recycle butane stream of line 3 represents an etherification zone "$C_4$ raffinate" and contains some (less than 2,000 ppm) product ether and feed alcohol and water from the etherification zone. This admixture is heated by a means not shown and then passed onto a fractionation tray 5 located at an intermediate point in the column. It is immediately subjected to a fractional distillation effect which drives the more volatile components upward. Essentially all of the entering admixture will therefore be vaporized and begin ascending through the column, while the $C_5$ hydrocarbons will begin moving downward.

The vapors formed in the lower portion of the column travel upward and enter into the zone 6 which contains an acid catalyst. An equilibrium amount of the compounds in the vapor enter into the liquid phase in this zone and come into contact with the catalyst. This causes a number of different reactions to occur with the result of these various reactions being the conversion of substantially all of the undesired contaminants into less volatile compounds which tend to migrate downward through the column with the liquid phase. For instance the mercaptans react with olefins and/or diolefins to form thioethers. Alcohol fed to the column can react with tertiary or secondary mono-olefins to form ethers. Any remaining isobutylene will react with the alcohol to form ethers. Water will react with olefins to form higher, less volatile alcohols. In addition any remaining olefins not consumed in an etherification or hydration reaction will tend to react to form dimers and trimers.

The paraffinic $C_4$ hydrocarbons are essentially inert in this environment and at the conditions employed in the column and gradually pass upward through the column in the rising vapor phase. They pass upward through more fractionation trays and are eventually withdraw as the overhead vapor of line 7. The overhead vapor is normally condensed through contact with a cooler not shown to form a liquid which is collected for withdrawal as the net overhead product, with a portion of the liquid being returned through line 9 as reflux liquid. As an alternative a condenser may be located in or directly above the top of the column. At the bottom of the column a liquid-phase bottoms stream comprising the dimers and thioethers and $C_5$ paraffins but substantially free of $C_4$ hydrocarbons is withdrawn via line 8. The compounds present in this stream are expected to be suitable for blending into a motor fuel stream. Heat is added to the bottom of the column by a reboiling means not shown. The term "substantially free" is intended to indicate the lower of 1.0 mole percent or one-tenth of the concentration of the indicated compound fed in the feed stream to the relevant column or conversion zone.

The term "substantially all" is intended to indicate at least 90 mole percent of the indicated compound or class of compounds. The term "rich" is intended to indicate a concentration greater than 50 mole percent and preferably greater than 75 mole percent.

The subject process can be adopted to a variety of feed streams. The basic criteria is that the feed stream comprises a paraffinic hydrocarbon which is not effected by the catalytic reactions performed to remove the contaminants. The preferred feed stream is rich in a single paraffinic hydrocarbon but the feed stream may comprise an admixture of two or more paraffins. Suitable paraffins include ethane, propane, butane, pentane and hexane. The feed stream must also contain olefinic hydrocarbons and mercaptans boiling in the same temperature range as the paraffins.

The subject process can be performed in a fractionation column of relatively normal design through the addition of a catalyst-retaining zone. A general range of operating conditions suitable for the catalytic distillation zone of the subject process include an overhead temperature of about 50 to 300 degrees C., preferably 70 to 150 degrees C., and a pressure as required to maintain at least a major portion (greater than 40 mole %) of the feed paraffinic hydrocarbons present as a liquid. Pressures in the general range of from about 200 to about 4000 kpa (30 to 600 psig) are believed suitable. The weight hourly space velocity (W.H.S.V.), defined as the net overhead liquid rate divided by the volume of catalyst in the column is preferably between about 0.1 and $10^{-1}$.

The catalyst(s) used in the subject process can be held in the catalytic distillation zone in a number of mechanically different apparatuses. The Catalyst could simply rest on a perforated tray with a screen covering the top of the catalyst bed. The catalyst may also be located in the downcomers of a tray or in a number of specialized retention volumes specifically designed for catalytic distillation as shown in U.S. Pat. Nos. 4,302,356; 4,439,350 and 4,443,559. It is also known that a resin catalyst can be present as a coating on various reactor internals including vapor-liquid contacting devices. It is preferred that the catalyst is retained in a structured packing which contributes to vapor-liquid contacting and which provides sufficient open volume to allow countercurrent vapor and liquid flow. The preferred apparatus for retaining the catalyst in the catalytic distillation zone is described in detail in U.S. Pat. No. 5,073,236 issued to A. P. Gelbein which is incorporated herein for its description as to the structure and use of these preferred catalyst packing systems. This apparatus is preferred because of its ability to disperse the catalyst throughout the catalytic distillation zone while also being highly effective in promoting vapor-liquid contacting and fractional distillation of the products from the reactants.

A wide variety of acid catalysts including zeolites can be employed in the subject invention. The catalysts can include a refractory oxide such as alumina, silica-alumina, or titania. A nonzeolitic molecular sieve (NZMS) such as described in U.S. Pat. Nos. 5,114,563 (SAPO) or 4,793,984 or a zeolite such as zeolite Y or zeolite Beta can be employed, but the preferred catalysts comprise an acidic resin catalyst. A macroporous acid form sulfonic comprise an acidic resin catalyst. A macroporous acid form sulfonic ion exchange resin as described in U.S. Pat. No. 2,922,822 having a degree of crosslinking of from about .5 to 60% is an example. Suitable resin catalysts are available commercially from a number of vendors. Sulfonated resin catalysts such as those sold by Rohm & Haas under the Amberlyst 36 trademark are especially preferred.

EXAMPLE

The performance of the invention was verified through a pilot plant test conducted using a once-through reactor. The feed to the reactor was a liquid phase hydrogen-free $C_4$ stream which was rich in $C_4$ paraffins and contained 2000 wt ppm isobutene, 350 ppm normal butene, 225 ppm methyl mercaptans and 290 ppm ethyl mercaptans. The reactor contained a single bed of catalyst and was operated at a temperature of 110degrees C. and a pressure of 2410 kPa (350 psig) which resulted in liquid-phase conditions. The feed was passed through the reactor at a LHSV of $2.0^{-1}$. The effluent of the reactor contained about 100 ppm isobutene, 200 ppm normal butene, 68 wt ppm methyl mercaptans and 170 ppm ethyl mercaptan. The effluent also contained thioethers and newly formed $C_8$-plus hydrocarbons. The thioethers were analyzed to be about 90% t-butyl sulfides and 10% n-butyl sulfides. Hence this nonoptimized test showed this procedure was effective in significantly decreasing the concentration of olefinic hydrocarbons and mercaptans in the feed stream by their conversion to thioethers and dimers and/or oligomers. Increased conversion can be achieved by conventional means such as increased residence time in a catalytic distillation column.

A preferred embodiment of the subject invention can accordingly be characterized as a process for preparing a feed stream for an etherification zone which comprises the steps of passing a first feed stream, which is rich in a $C_3$ to $C_6$ feed paraffin and also comprises a mercaptan (possibly several different mercaptans of different carbon numbers) and an olefinic hydrocarbon concentration less than about 5 volume %, into a catalytic distillation column operated at conditions which effect the separation of the compounds present in the column into a net overhead stream, which comprises substantially all of the paraffins which enter the column and is substantially free of mercaptans, and a net bottoms stream which comprises higher boiling, relative to the paraffins, sulfur compounds and dimers of the olefinic hydrocarbons present in the feed stream; passing a second feed stream, which is rich in the feed hydrocarbon and comprises an ether, an alcohol and water into the catalytic distillation column; contacting, in the substantial absence of hydrogen the olefins, mercaptans, ether, alcohol and water present in the first and second feed streams with a bed of an acid catalyst located in the catalytic distillation column and maintained at conditions which effect the production of thioethers by the reaction of substantially all of the mercaptans present in the first feed stream with olefinic hydrocarbons originally present in the first feed stream and the dimerization of olefinic hydrocarbons; removing said net bottoms stream and said net overhead stream from the column; and, passing the net overhead stream into hydrocarbon conversion zone which produces an olefinic hydrocarbon used in said etherification zone.

What is claimed:

1. A process for the removal of mercaptans from a paraffin-rich stream which comprises the steps:

(a) passing a feed stream, comprising one or more $C_3$ to $C_6$ feed paraffin(s), and also comprising a mercaptan and an olefinic hydrocarbon at a concentration of less than 5 volume % each, with the olefinic hydrocarbon having the same number of carbon atoms per molecule as the feed paraffin(s), into a catalytic distillation column operated at conditions which effect the separation of the compounds present in the column into a net overhead stream, which comprises substantially all of the paraffins which enter the column in the feed stream, and a net bottoms stream which comprises sulfur compounds and dimers of the olefinic hydrocarbons present in the feed stream;

(b) contacting the compounds present in the feed stream, in the substantial absence of hydrogen, with a bed of catalyst located in the catalytic distillation column and maintained at conditions which effect the production of thioethers by the reaction of mercaptans in the feed stream with olefinic hydrocarbons present in the feed stream and the dimerization of olefinic hydrocarbons; and, (c) removing said net bottoms stream and said net overhead stream from the column.

2. The process of claim 1 further characterized in that the feed stream comprises an oxygenate.

3. The process of claim 1 further characterized in that the feed stream comprises an alcohol.

4. The process of claim 1 further characterized in that the feed stream is rich in $C_5$ paraffins.

5. The process of claim 1 further characterized in that the feed stream is rich is $C_4$ paraffins.

6. The process of claim 1 further characterized in that the catalyst comprises an acid resin.

7. A process for the removal of mercaptans from a paraffin-rich stream which comprises the steps of passing a feed stream, which is rich in a $C_3$ to $C_6$ feed paraffin and comprises one or more mercaptans and an olefinic hydrocarbon having the same number of carbon atoms as the feed paraffin, into a catalytic distillation column and contacting the compounds present in the feed stream with a bed of an acid catalyst located in the catalytic distillation column and maintained at conditions which effect the production of thioethers by the reaction, in the substantial absence of hydrogen, of substantially all of the mercaptans present in the feed stream with olefinic hydrocarbons originally present in the feed stream and the dimerization of olefinic hydrocarbons, with the catalytic distillation column being operated at conditions which effect the separation of the compounds present in the column into a net overhead stream, which comprises substantially all of the paraffins which enter the column and is substantially free of mercaptans, and a net bottoms stream which comprises sulfur compounds and dimers of the olefinic hydrocarbons present in the feed stream, and removing said net bottoms stream and said net overhead stream from the column.

8. The process of claim 7 further characterized in that the feed stream also comprises an alcohol, which is converted to an ether and removed from the column in the net bottoms stream.

9. The process of claim 7 further characterized in that the feed stream also comprises water, which is converted to an alcohol within the column and removed in the net bottoms stream.

10. A process for preparing a feed stream for an etherification zone which comprises the steps:

(a) passing a first feed stream, which is rich in a $C_3$ to $C_6$ feed paraffin and also comprises a mercaptan and an olefinic hydrocarbon having the same number of carbon atoms as the feed paraffin at a concentration less than about 5 volume %, into a catalytic distillation column operated at conditions which effect the separation of the compounds present in the column into a net overhead stream, which comprises substantially all of the paraffins which enter the column and is substantially free of mercaptans, and a net bottoms stream which comprises sulfur compounds and dimers of the olefinic hydrocarbons present in the feed stream;

(b) passing a second feed stream, which is rich in the feed hydrocarbon and comprises an ether, and an alcohol into the catalytic distillation column;

(c) contacting, in the substantial absence of hydrogen, the olefins, mercaptans, ether, and alcohol present in the first and second feed streams with a bed of an acid catalyst located in the catalytic distillation column and maintained at conditions which effect the production of thioethers by the reaction of mercaptans present in the first feed stream with olefinic hydrocarbons originally present in the first feed stream and the dimerization of olefinic hydrocarbons;

(d) removing said net bottoms stream and said net overhead stream from the column; and, (e) passing the net overhead stream into a hydrocarbon conversion zone which produces an olefinic hydrocarbon used in said etherification zone.

\* \* \* \* \*